United States Patent [19]

Hoffman et al.

[11] Patent Number: 5,409,825
[45] Date of Patent: Apr. 25, 1995

[54] EXPANSION OF HUMAN HEMATOPOIETIC PROGENITOR CELLS IN A LIQUID MEDIUM

[76] Inventors: Ronald Hoffman, 5305 N. Pennsylvania St.; John Brandt, 6312 Douglas Rd., both of Indianapolis, Ind. 46220

[21] Appl. No.: 133,093

[22] PCT Filed: Apr. 9, 1992

[86] PCT No.: PCT/US92/02895

§ 371 Date: Oct. 12, 1993

§ 102(e) Date: Oct. 12, 1993

[87] PCT Pub. No.: WO92/18615

PCT Pub. Date: Oct. 29, 1992

Related U.S. Application Data

[63] Continuation-in-part of Ser. No. 682,344, Apr. 9, 1991, abandoned.

[51] Int. Cl.$^6$ .......................... C12N 5/00; C12N 5/02; C12N 5/08
[52] U.S. Cl. ............................. 435/240.1; 435/240.2; 435/240.21; 435/240.25
[58] Field of Search ............. 435/240.1, 240.2, 240.21, 435/240.25

[56] References Cited

U.S. PATENT DOCUMENTS

| | | | |
|---|---|---|---|
| 5,061,620 | 10/1991 | Tsukamoto et al. | 435/7.21 |
| 5,073,627 | 2/1991 | Curtis et al. | 530/351 |
| 5,087,570 | 2/1992 | Weissman et al. | 435/240.1 |
| 5,199,942 | 4/1993 | Gillis | 604/4 |
| 5,256,560 | 10/1993 | Lawman et al. | 435/240.2 |
| 5,258,367 | 11/1993 | Bazer et al. | 514/6 |

OTHER PUBLICATIONS

Brandt et al. (1989) Blood 74(7) suppl, abstract 420. In vitro characterization of human marrow cells with long term hematopietic repopulating ability.
Brandt, J., et al., 1990, Journal of Clinical Investigation, 86(3):932–941.
Williams, D. E., et al., 1990, Experimental Hematology, 18(6):615, No. 256.
Gualtieri, R. J., et al., 1984, Blood, 64(2): 516–525.
Kobayashi, M., et al., 1989, Blood, 73(7):1836–1841.
Svour, E. F., et al., 1991, Blood Cells, 17(2):287–295.
Srour, E. F., et al., 1992, The Journal of Immunology, 148(3):815–820.
Brandt, J., et al., 1992, Blood, 79(3):634–641.
Bruno, E., et al., 1989, Blood, 73(3): 671–677.
Brandt, J., et al., 1988, Journal of Clinical Investigations 82(2):1017–1027.
McNiece, I. K., et al., 1991 Experimental Hematology, 19:226–231.
Bruno E. et al., 1989, Experimental Hematology, 17(10):1038–1043.
Briddell, R. A., et al., 1989, Blood 74(1):145–151.
Lu, L., et al., 1988, British Journal of Hematology, 70(2):149–156.
Briddell, R. A., et al., 1990, Blood, 76(3):516–522.
Verfaillie, C., et al., 1991, Blood, 77(2):263–270.
Antony, A. C., et al., 1991, Journal of Clinical Investigation, 87:313–325.
Quesenberry, P., et al., 1991, Journal of Cellular Biochemistry, 45:273–278.
Bruno, E., et al., 1991, Blood, 77(11):2339–2346.
Srour, E. F., et al., 1991, Cytometry 12(2):179–183.
Brandt, J., et al., 1988, Advances in Experimental Medicine and Biology, 241:165–173.
Brandt, J., et al., 1990, in Dainiak, N., et al., Eds., *Progress in Clinical and Biological Research*, Wiley-Liss, Inc., publishers, pp. 29–36.

(List continued on next page.)

*Primary Examiner*—Robert A. Wax
*Assistant Examiner*—William W. Moore
*Attorney, Agent, or Firm*—Bertram I. Rowland; Pamela J. Sherwood

[57] ABSTRACT

A process for supporting hematopoietic progenitor cells in a culture medium which contains at least one cytokine effective for supporting the cells, and preferably, is essentially free of stromal cells.

5 Claims, No Drawings

OTHER PUBLICATIONS

Ponting, I. L. O., et al., 1991, Growth Factors, 4:165–173.

Lu, L., et al., 1988, Behring Institute Mitteilungen, 83:181–187.

Hoffman, R., et al., 1990, The Yale Journal of Biology and Medicine 63(5):411–418.

Hoffman, R., et al., 1990, Progress in Clinical and Biological Research 338:75–103.

Hoffman, R., et al., 1990, Progress in Clinical and Biological Research, 35:199–215.

J. Clin. Invest., vol. 86, issued Sep. 1990, J. Brandt et al., "Cytijube-dependent long-term culture of highly enriched precursors of hematopoietic progenitor cells from human bone marrow", pp. 932–941, see entire document.

Exp. Hematol., vol. 18, Issued 1990, D. E. Williams et al., "Enhanced biological activity of a human GM–CSF/IL-3 fusion protein", p. 615, see entire document.

Blood, vol. 64, No. 2, issued Aug. 1984, R. J. Gualtieri et al., "Hematopoietic regulatory factors produced in long-term murine bone marrow cultures and the effect of in vitro irradiation", pp. 516–525, see entire document.

Blood, vol. 73, No. 7, issued 15 May 1989, M. Kobayashi et al., "Interleukin-3 is significantly more effective than other colony-stimulating factors in long-term maintenance of human bone marrow-derived colony-forming cells in vitro", pp. 1836–1841, see entire document.

Blood Cells, vol. 17, No. 2, issued 29 Apr. 1991, E. F. Srour et al., "Human CD34+HLA–DR–bone marrow cells contain progenitor cels capable of self-renewal, mutlilineage differentation, and long-term in vitro hematopoiesis", pp. 287–295, see entire document.

J. Immunol., vol. 148, No. 3, issue 01 Feb. 1992, E. F. Srour et al., "Relationship between cytokine-dependent cell cycle progression and MHC class II antigen expression by human CD34+HLA–DR–bone marrow cells", pp. 815–820, see entire document.

Blood, vol. 79, No. 3, issued 01 Feb. 1992, J. Brandt et al., "Role of c–kit ligand in the expansion of human hematopoietic progenitor cells", pp. 634–641, see entire document.

EXPANSION OF HUMAN HEMATOPOIETIC PROGENITOR CELLS IN A LIQUID MEDIUM

This application is a continuation-in-part of U.S. Ser. No. 07/682,344, filed Apr. 9, 1991, now abandoned.

This invention relates to a system and process for supporting human stem cells and more particularly the present invention relates to supporting hematopoietic stem cells for use in bone marrow transplant patients.

Mammalian hematopoiesis has been studied in vitro through the use of various long-term marrow culture systems (3, 10–12). Dezter and co-workers (3) described a murine system from which CFU-S an CFU-GM could be assayed for several months, with erythroid and megakaryocytic precursors appearing for a more limited time. Maintenance of these cultures was dependent on the formation of an adherent stromal cell layer composed of endothelial cells, adipocytes, reticular cells, an macrophages. These methods were soon adapted for the study of human bone marrow. Human long-term culture systems were reported to generate assayable hematopoietic progenitor cells for 8 or 9 weeks (10, 11) and, later, for up to 20 weeks (12, 13). Such cultures are again relying on the pre-establishment of a stromal cell layer which is frequently reinoculated with a large, heterogeneous population of marrow cells. Hematopoietic stem cells have been shown to home and adhere to this adherent cell multilayer before generating and releasing more committed progenitor cells (1, 14, 15). Stromal cells are thought to provide not only a physical matrix on which stem cells reside, but also to produce membrane-contact signals and/or hematopoietic growth factors necessary for stem cell proliferation and differentiation (4, 5, 16, 17). This heterogeneous mixture of cells comprising the adherent cell layer presents an inherently complex system from which the isolation of discrete variables affecting stem cell growth has proven difficult.

Recently, a study was conducted by McNiece and Langley which examined the stimulatory effect of recombinant human stem cell factor (MGF) on human bone marrow cells alone and in combination with recombinant human colony stimulating factors, GM-CSF, IL-3 and erythropoietin. The results showed that MGF stimulation of low density non-adherent, antibody depleted CD34+ cells suggests that MGF directly stimulates progenitor cells capable of myeloid and erythroid differentiation (18).

In accordance with an aspect of the present invention there is provided a process for supporting mammalian bone marrow cells wherein such cells are maintained in a culture medium essentially free of stromal cells and which includes at least one cytokine effective for supporting such cells.

Preferred embodiments of this aspect of the present invention provide a process for supporting bone marrow cells which are hematopoietic stem cells, a process for supporting bone marrow cells which are hematopoietic progenitor cells and a process for supporting bone marrow cells which are CD34+DR−CD15− cells.

In addition, this invention provides that at least one cytokine be selected from the following cytokines: Interleukin (IL)-1, IL-3, IL-6, granulocyte/macrophate-colony stimulating factor (GM-CSF), human or murine stem cell factor, sometimes referred to as human or murine mast cell growth factor (MGF) and a fusion protein of GM-CSF/IL-3 (FP). Further, this invention provides particularly preferred embodiments wherein the cytokine MGF is included as the sole cytokine or in combination with at least one other cytokine.

In accordance with another aspect of the present invention there is provided a process for supporting mammalian bone marrow cells wherein such cells are maintained in a culture medium containing a combination of cytokines effective for supporting such cells. Preferably, the bone marrow will be supported in a culture medium which is essentially free of stromal cells.

Another aspect of the present invention provides for a process of supporting mammalian bone marrow cells wherein such cells are maintained in a culture medium which is essentially free of serum and of stromal cells. This system allows for preferred expansion of progenitor cell numbers and enables the identification of which cytokines specifically affect progenitor cell expansion.

Another aspect of the present invention provides for a process of supporting mammalian bone marrow cells wherein such cells are maintained in a culture system which is essentially a serum-free long-term suspension human bone marrow. This system allows for preferred expansion of human progenitor cell numbers and enables the identification of which cytokines specifically affect human progenitor cell expansion. Preferably, the medium is essentially free of stromal cells.

Additional preferred embodiments of this invention provide a process for supporting bone marrow cells which are hematopoietic stem cells, a process for supporting bone marrow cells which are hematopoietic progenitor cells and a process for supporting bone marrow cells which are CD34+DR−CD15− cells.

Preferably, the culture medium will contain at least one of the following cytokine combinations: IL-1/IL-3; IL-3/IL-6; IL-3/KGF; IL-3/GM-CSF; MGF/FP. Applicant has found that such combinations provide for an improved rapid expansion of the cells population.

The term "supporting" with respect to stem cells and other progenitor cells means maintaining and/or expanding and/or promoting some differentiation of such cells.

The following are representative examples of cytokines which may be employed in the present invention: IL-1 in an amount effective to support the cells. Generally, such amount is at least 20 pg/ml and need not exceed 1 ng/ml, preferably 1 ng/ml; IL-6 in an amount effective to support the cells. Generally, such amount is at least 20 pg/ml and need not exceed 1 ng/ml, preferably 1 ng/ml; IL-6 in an amount effective to support the cells. Generally, such amount is at least 1 ng/ml and need not exceed 50 ng/ml preferably 10 ng/ml; IL-3 in an amount effective to support the cells. Generally, such amount is at least 500 pg/ml and need not exceed 2 ng/ml preferably 500 pg/ml; GM-CSF in an amount effective to support the cells. Generally, such amount is at least 100 pg/ml and need not exceed 1 ng/ml, preferably 200 pg/ml; MGF in an amount effective to support the cells. Generally, such amount is at least 10 ng/ml and need not exceed 50 ng/ml, preferably 50 ng/ml; and FP in an amount effective to support the cells. Generally, such amount is at least 1 ng/ml and need not exceed 10 ng/ml, preferably 10 ng/ml. Such cytokines may be employed alone or in combination with each other.

The use of a cytokine in the absence of stromal cells is particularly suitable for expanding the mammalian bone marrow stem cells and in particular progenitor cells. The cells which are supported in accordance with the present invention are preferably of human origin.

In accordance with a preferred aspect of the present invention, a cell population which is supported in accordance with the present invention is that which is positive for CD34 antigen and is negative for HLA-DR and is also negative for CD15.

Specifically, this aspect of the present invention provides for cell population of CD34+DR−CD15− supported in accordance with the process described above, where the population has doubled in a period of time which does not exceed 15 days. Preferably, the population has doubled in 7 to 15 days.

In accordance with another aspect, the present invention provides for a cell population of bone marrow cells supported in accordance with the process described herein, where the population has doubled in a period of time which does not exceed 15 days. Preferably, the population has doubled in 7 to 15 days.

In accordance with another aspect, the present invention provides for a cell population of hematopoietic stem cells supported in accordance with the process described herein, wherein the population has doubled in a period of time which does not exceed 15 days. Preferably, the population has doubled in 7 to 15 days.

In accordance with another aspect, the present invention provides for a cell population of hematopoietic progenitor cells supported in accordance with the process described herein, where the population has doubled in a period of time which does not exceed 15 days. Preferably, the population has doubled in 7 to 15 days.

Another aspect of the present invention provides for a composition comprised of an expanded bone marrow cell culture which is essentially free of stromal cells, the culture also contains at least one cytokine and the culture's cell population has doubled in a time not exceeding 15 days. Preferably, the cell population will have doubled in at least 7 and not exceeding 15 days.

Human long-term bone marrow cultures (LTBMC) have been though to require the formation of an adherent stromal cell layer for sustained in vitro hematopoiesis. The CD34+DR−CD15− population of human marrow cells are capable of multilineage differentiation, self-renewal, and of initiating LTBMC in the absence of stromal cells for up to 12 weeks when continually supplied with cytokines. Preferably the cytokine supplied is interleukin-3 (IL-3). The effects of stromal cells on CD34+DR−CD15− cells in the presence and absence of IL-3 in LTBMC have been observed. Suspension cultures of CD34+DR−CD15− cells in the absence of stroma were characterized by sustained hematopoiesis for 10–12 weeks as demonstrated by a high degree of cellular proliferation and multilineage progenitor cell expansion when supplied with IL-3. No adherent layer formed in these cultures, and IL-3 was necessary for their survival beyond one week. Such stroma-free cultures produced 500 to more than 900 assayable CFU-GM over a 12-week period, while BFU-E were generated for 1–3 weeks. By contrast, 4-week-old stromal cultures recharged with autologous CD34+DR−CD15− cells both in the presence and absence of exogenous IL-3 generated far fewer (100–500) assayable colony-forming cells for only six weeks, and production of nonadherent cells was greatly reduced over the 12-week observation period. Stromal cultures supplemented with IL-3 but not re-seeded with CD34+DR−CD15− cells behaved similarly to those to which sorted cells were added. These data suggest that marrow stromal cells modulate the effects of cytokines on hematopoietic stem cell development and proliferation and elaborate signals that both promote and dampen in vitro hematopoieses.

An additional aspect of the present invention provides for a composition comprised of an expanded bone marrow cell culture which contains a combination of cytokines and the cultures cell population has doubled in a time not to exceed 15 days. Preferably the cell population has doubled in at least 7 and not exceeding 15 days. It is also preferable, that the cell culture be essentially free of stromal cells.

As previously indicated, the present invention is particularly applicable to bone marrow cells that are positive for CD34 antigen but which do no express HLA-DR, CD15 antigens in that it is believed that such cell population is believed to be closely associated with human hematopoietic stem cells, but it is to be understood that the present invention is not limited to supporting such a cell population.

The cells supported in accordance with the present invention may be used in a variety of ways. For example, such cells may be employed as part of a bone marrow transfer procedure.

Expanded hematopoietic stem cell populations can be used as grafts for marrow transplantation to treat malignancies, bone marrow failure states and cogenital metabolic, immunologic and hematological disorders. Marrow samples will be taken from patients with cancer and CD34+DR−CD15− cells isolated by means of density centrifugation, counterflow centrifugal elutriation, monoclonal antibody labeling and fluorescence activated cell sorting. The stem cells in this cell population will then be expanded in vitro and will serve as a graft for autologous marrow transplantation. The graft will be infused after the patient has received curative chemo-radiotherapy.

Expanded stem cell populations can also be utilized for in utero transplantation during the first trimester of pregnancy. Fetuses with metabolic and hematologic disorders will be diagnosed prenatally. Marrow will be obtained from normal individuals and CD34+DR−CD15− cells will be obtained by the methods described previously and expanded in vitro. They will then be administered to the fetus by in utero injection. A chimera will be formed which will lead to partial but clinically significant alleviation of the clinical abnormality.

The invention will be further described with respect to the following examples; however, the scope of the invention is not to be limited thereby:

EXAMPLE 1

A. Materials and Procedures

Prior to performing any procedures, informed consent was obtained from all volunteers according to the guidelines of the Human Investigation Committee of the Indiana University School of Medicine.

Cell Separation Techniques

Bone marrow aspirates were collected from the posterior iliac crests of normal volunteers Low-density mononuclear bone marrow (LDBM) cells were obtained by density centrifugation of the heparinized marrow over Ficoll-Pague (Pharmacia Fine Chemicals, Piuscataway, N.J.) at 500 g for 25 min. LDBM cells were suspended in PBS-EDTA (PBS, pH 7.4, containing 5% FBS, 0.01% EDTA wt/vol, and 1.0 g/liter D-glucose) and injected into an elutriator system at 10° C. at a rotor speed of 1,950 rpm using a JA-17 rotor and standard separation chamber (Beckman Instruments, Inc., Palo Alto, Calif.). A fraction of the LDBM eluted at a flow rate of 12–14 ml/min (FR 12–14), enriched for hematopoietic precursors, was collected as previously described (2).

Long-term Marrow Cultures Free of Stromal Cells

Plastic 35-mm tissue culture dishes were seeded with $2 \times 10^6$ LDBM cells in 1 ml of Iscove's with 10% FBS and $2 \times 10^{-5}$ M methylprednisolone. Cultures were incubated at 37° C. in 100% humidified atmosphere containing 5% $CO_2$ in air and fed weekly by total replacement of media. Stromal cells were confluent by 4–6 wk. The stromal cultures were then irradiated with 1,500 rad, the media were replaced, and the cultures were inoculated with $5 \times 10^3$ sorted bone marrow cells from autologous donors. The media in these cultures were removed at 7–10 d intervals and replaced with fresh media. Suspended, nonadherent cells were then counted and assayed for progenitors.

Long-term Suspension Cultures

Plastic 35-mm tissue culture dishes containing 1 ml of Iscove's with 10% FBS were inoculated with stromal cell free long term marrow cells containing $5 \times 10^3$ cells obtained by sorting and incubated at 37° C. in 100% humidified atmosphere containing 5% $CO_2$ in air. At this time, and every 48 h thereafter, cultures received nothing (1% BSA/PBS), 2.5 U/ml IL-1a, 50 U/ml IL-3, 75 U/ml IL-6, 12.5 U/ml GM-CSF, or combinations of the above. At 7d intervals, cultures were demi-depopulated by removal of one-half the culture volume which was replaced with fresh media. Cells in the harvested media were counted, transferred to slides for staining and morphological examination, and assayed for various progenitor cells.

Hematopoietic Growth Factors

All cytokines were obtained from the Genzyme Corp., Boston, Mass. Recombinant IL-1a and In-3 each had a specific activity of $10^8$ CFU/mg protein, while that of IL-6 was $10^7$ and granulocyte/macrophage colony-stimulating factor (GM-CSF) $5 \times 10^7$ CFCc/mg protein.

Two- and Three-color Cell Sorting

FR 12–14 cells were incubated with mouse monoclonal anti-HPCA-1 (CD34) of the $IgG_1$ subclass (Becton Dickinson Immunocytometry Systems, San Jose, Calif.), washed, and stained with Texas red-conjugated, subclass-specific goat anti-mouse $IgG_1$ (Southern Biotechnology Associates, Inc., Birmingham, Ala.). Cells were next incubated with mouse serum to block any unbound active sites on the second-step antibody. Cells were finally stained with phycoerythrin-conjugated mouse anti-HLA-DR either alone or in combination with FITC-conjugated CD33 (My9, Coulter Immunology, Hialeah, Fla.), CD15 (Leu-M1), or CD71 (transferring receptor) (Becton Dickinson Immunocytometry Systems). CD15 is present on cells of the granulocytic and monocytic lineages, and an anti-CD15 monoclonal antibody was employed in the hope of eliminating these cellular components from the cell populations (6). CD71 is present on actively proliferating cells and an anti-CD71 antibody was utilized to separate actively proliferating cells from more quiescent marrow elements (7). Controls consisted of the corresponding isotype-matched, nonspecific myeloma proteins used in parallel with staining monoclonal antibodies. Cells were stained at a concentration of $2 \times 10^7$/ml and washed after each step in 1% BSA in PBS. A temperature of 4° C. was maintained throughout the procedure.

Immediately after staining, cells were sorted on a Coulter Epics 753 dual-laser flow cytometry system (Coulter Electronics, Inc., Hialeah, Fla.). Texas red was excited by 590 nm light emitted from a rhodamine 6G dye laser. FITC and phycoerythrin were excited using the 488 nm wavelength from a dedicated 6-W argon laser. Sorting windows were first established for forward angle light scatter (FALS) and Texas red fluorescence. Positivity for each fluorochrome was defined as fluorescence >99% of that of the controls. Cells were next gated on the presence or absence of detectable HLA-DR-phycoerythrin and CD33-FITC, CD15-FITC, or CD71-FITC.

Hematopoietic Progenitor Cells Assays

Cells were suspended at various concentrations in 35-mm plastic tissue culture dishes (Costar Data Packaging, Cambridge, Mass.) containing 1 ml of 30% FBS, $5 \times 10^{-5}$ M 2-mercaptoethanol, 1 U human purified erythropoietin (50 U/mg protein, Toyobo Colo. Ltd., Osaka, Japan), 50 U GM-CSF, and 1.1% methylcellulose in Iscove's modified Dulbecco's medium. The cultures were incubated at 37° C. in a 100% humidified atmosphere containing 5% $Co_2$ in air. After 14 d, erythropoietic bursts (BFU-E), granulocyte-macrophage (CFU-GM), and mixed lineage (CFU-GEMM) colonies were scored in situ on an inverted microscope using standard criteria for their identification (2).

High proliferative potential colony-forming cell (HPP-CFC)-derived colonies were enumerated after 28 d in culture according to the recently published criteria of McNiece and co-workers (8). The human HPP-CFC derived colony is a late-appearing, very large (0.5 mm or more in diameter) colony composed primarily of granulocytes with a lesser number of monocytes; cell numbers frequently exceed 50,000.

Cells removed from suspension cultures were assayed for CFU-megakaryocyte (CFU-MK) colonies using the serum-depleted method described in detail by Bruno et al. (9) $5 \times 10^3$ cells per point were suspended in a 1-ml serum-substituted fibrin clot with 100 U of IL-3 in 35-mm culture dishes and incubated at 37° C. in a 100% humidified atmosphere containing 5% $CO_2$ in air. At 18–24 d, cultures were fixed in situ and stained using rabbit anti-human platelet glycoprotein antisera, and fluorescein-conjugated goat F(ab')2-specific anti-rabbit IgG (Tago, Inc., Burlingame, Calif.) and megakaryocyte colonies were enumerated on a Zeiss fluorescence microscope (Carl Zeills, Inc., New York, N.Y.). A positive colony was defined as a cluster of three or more fluorescent cells.

B. Experiments

A liquid culture system supplemented with repeated 48-hourly cytokine additions was utilized to study cell populations. Total cell production by both CD34+DR−CD15− and CD34+DR−CD71− cells is shown in Tables I and II while assayable CFU-GM in these cultures over time are recorded in Tables III and IV. In the absence of exogenous cytokines, total cell numbers declined over a 2-wk period and assayable CFU-GM persisted for only 1 or 2 wk. The repeated addition of IL-1a did not significantly enhance total cell production or generation of CFU-GM by either CD34+DR−CD15− or CD34+DR−CD71− cells. IL-6 did not alter total cell numbers or numbers of assayable CFU-GM in cultures initiated with CD34+DR−CD71− cells. By contrast, IL-6 increased total cell numbers over seven fold by week 3 by CD34+DR−CD15− initiated cultures but did not appreciably extend the interval over which CFU-GM were detected. In both sets of experiments, GM-CSF promoted increased total cell production for 6 wk, by which time cell numbers represented 20-80 times the number present in the initial seeding populations. Assayable CFU-GM persisted for 3-4 wk and cumulatively surpassed those assayable in the initial populations. The single most effective cytokine in terms of promoting cellular expansion, increasing the number of CFU-GM, and lengthening the duration of time over which CFU-GM were assayable was IL-3. Both CD34+DR−CD15− and CD34+$^{DR}$−CD71− cells experienced 200-fold increases in cell numbers by day 28, and, after 1 or 2 wk in culture, contained equal or slightly greater numbers of CFU-GM than present in the initial inoculi. Assayable progenitors were produced for 4-5 wk in the system when maintained with IL-3, and viable cell counts remained high at 8 wk. IL-1a or IL-6 prolonged and enhanced these effects when added in combination with IL-3. CFU-GM were assayable after 8 wk in suspension culture after continued treatment with these two cytokine combinations. No adherent cell layer was established in any of the suspension cultures over the 8 wk period of observation.

In a separate experiment, CD34+DR−CD71− cells were grown in this suspension culture system in the presence of a combination of both IL-3 and IL-6 and assayed for CFU-MK from days 7 through 28 of culture. CFU-MK were detected over this 28 d period (Table V). Utilizing this IL-3/IL-6 cytokine combination, the ability of CD34+DR−CD15+ and CD34+DR−CD71+ cells to sustain long-term hematopoiesis was compared to that of the CD34+DR−CD15− and CD34+DR−CD71− fractions (Table VI). Both the CD15-positive and CD71-positive calls failed to generate CFU-GM after 2 wk, and the CD71-positive population, which initially included the overwhelming majority of BFU-E, failed to produce assayable BFU-E after only 7 d in culture.

Morphological analysis of the cells in these suspension cultures during the period of observation revealed changes in the cellular composition of the populations following the addition of various cytokines (Tables VII and VIII). IL-1a-and IL-6-containing cultures behaved very similarly to the control samples. Cultures to which no cytokines were added were composed of 90-100% blasts after 1 wk; the CD34+DR−CD15− cells did not survive 2 wk in the absence of cytokine whereas the CD34+DR−CD71− initiated cultures were composed of 40% blasts and 60% monocytes by week 2. Cultures receiving IL-1a had a similar cellular composition. IL-6 facilitated some differentiation to the granulocytic series by both cell populations; the CD34+DR−CD15− cells produced a significant number of mature granulocytic elements by week 2. GM-CSF, as well as IL-3, reduced the percentage of blasts in these suspension cultures appreciably by day 7. GM-CSF-containing cultures of CD34+DR−CD15− cells consisted primarily of metamyelocytes through 4 wk, with a shift to monosytes occurring by week 6.

IL-3 was unique in that, at 3 wk, suspension cultures initiated by either CD34+DR−CD15− or CD34+DR−CD71− cells were composed of 48% basophils in the presence of this growth factor (Tables VII and VIII). Addition of IL-1a or IL-6 did not alter this trend, all IL-3-containing cultures being composed of about 50% basophils by 3 wk and retaining significant numbers of basophils throughout the duration of culture.

The cellular composition of hematopoietic colonies assayed from aliquots of the suspension cultures was comparable to those assayed from the original sorted populations with a few notable exceptions. Blast cell colonies, as well as HPP-CFC-derived colonies, were routinely obtained by directly assaying CD34+DR−CD15− or CD34+DR−CD71− cells while these colony types were not observed in subsequent clonal assays of cellular aliquots obtained from the long-term liquid cultures. Distribution of GM colony subtypes, however, remained fairly consistent with roughly 40% being granulocyte/macrophage, 40% monocyte/macrophage, and 20% basophil or eosinophil colonies in either assays initiated with sorted cells of those initiated on days 7 through 42 of liquid culture. These CFU-GM-derived colonies ranged in size from 100 to 2,000 cells with the average colony containing between 200 tp 400 cells. After 8 wk of suspension culture, monosyte/macrophage colonies were the predominant colony type observed in the clonal assays.

TABLE I

Total Cell production of CD34+, DR−, CD15− Cells after Addition of Various Cytokines

| Cytokine | Day | | | | | | | |
|---|---|---|---|---|---|---|---|---|
| | 0 | 7 | 14 | 21 | 28 | 35 | 42 | 56 |
| | viable cell count × 10³ | | | | | | | |
| None | 5 | 1 | 4 | 0 | 0 | 0 | 0 | 0 |
| Il-1 | 5 | 2 | 2 | 0 | 0 | 0 | 0 | 0 |
| IL-3+ | 5 | 53 | 140 | 591 | 1,085 | 533 | 678 | 781 |
| IL-6§ | 5 | 3 | 4 | 36 | 26 | 16 | 0 | 0 |
| GM-CSF° | 5 | 8 | 14 | 44 | 169 | 213 | 118 | 0 |
| IL-1a/IL-3 | 5 | 32 | 167 | 556 | 1,360 | 1,387 | 758 | 1,069 |
| IL-6/IL-3 | 5 | 47 | 171 | 471 | 854 | 1,440 | 1,200 | 1,216 |

Total cells = cells/ml culture (½)$^n$, where n = number of previous demi-depopulations.

*2.5 U/ml recombinant human IL-1a were added every 48 h; specific activity 10⁸ CFU/mg protein.

+50 U/ml recombinant human IL-3 were added every 48 h; specific activity 10⁸ CFU/mg protein.

§75 U/ml recombinant human IL-6 were added every 48 h; specific activity 10⁷ CFU/mg protein.

°12.5 U/ml recombinant human GM-CSF were added every 48 h; specific activity 5 × 10⁷ CFU/mg protein.

TABLE II

Total Cell Production of CD34+, DR−. CD71− Cells after Addition of Various Cytokines

| Cytokine | Day | | | | | | | |
|---|---|---|---|---|---|---|---|---|
| | 0 | 7 | 14 | 21 | 28 | 35 | 42 | 56 |
| | viable cell count × 10³ | | | | | | | |
| None | 5 | 1 | 2 | 0 | 0 | 0 | 0 | 0 |
| IL-1* | 5 | 3 | 0 | 0 | 0 | 0 | 0 | 0 |
| IL-3+ | 5 | 40 | 226 | 964 | 746 | 1,190 | 1,120 | 851 |
| IL-6§ | 5 | 1 | 2 | 0 | 0 | 0 | 0 | 0 |
| GM-CSF° | 5 | 3 | 34 | 44 | 45 | 445 | 438 | 0 |
| IL-1a/IL-3 | 5 | 23 | 202 | 684 | 1,112 | 835 | 800 | 1,067 |

Total cells = cells/ml culture (½)$^n$, where n = number of previous demi-depopulations.

*2.5 U/ml recombinant human IL-1a were added every 48 h; specific activity 10⁸ CFU/mg protein.

+50 U/ml recombinant human IL-3 were added every 48 h; specific activity 10⁸ CFU/mg protein.

§75 U/ml recombinant human IL-6 were added every 48 h; specific activity 10⁷ CFU/mg protein.

°12.5 U/ml recombinant human GM-CSF were added every 48 h; specific activity 5 × 10⁷ CFU/mg protein.

TABLE III

Total CFU-GM Production by CD34+, DR−, CD15−
Cells after Addition of Various Cytokines

| Cytokine | Week 1 | 2 | 3 | 4 | 5 | 6 | 7 |
|---|---|---|---|---|---|---|---|
| | CFU-GM/ml culture | | | | | | |
| None | 40 | 0 | 0 | 0 | 0 | 0 | 0 |
| IL-1* | 22 | 14 | 0 | 0 | 0 | 0 | 0 |
| IL-3+ | 432 | 696 | 591 | 325 | 0 | 0 | 0 |
| IL-6§ | 42 | 242 | 96 | 0 | 0 | 0 | 0 |
| GM-CSF° | 273 | 200 | 219 | 0 | 0 | 0 | 0 |
| IL-1a/IL-3 | 254 | 397 | 444 | 408 | 139 | 152 | 64 |
| IL-6/IL-3 | 98 | 342 | 236 | 768 | 864 | 1,080 | 384 |

Total CFU-GM = CFU-GM/ml culture $(1.2)^n$, where n = number of previous demi-populations.
Cells were seeded at $5 \times 10^3$/ml. CFU-GM in initial (day 0) population = 555/5 × $10^3$ cells. Colonies grown in bethylcellulose containing 50 U/ml GM-CSF and enumerated after 14 d.
*2.5 U/ml recombinant human IL-1α were added every 48 h; specific activity $10^8$ CFU/mg protein.
+50 U/ml recombinant human IL-3 were added every 48 h; specific activity $10^8$ CFU/mg protein.
§75 U/ml recombinant human IL-6 were added every 48 h; specific activity $10^7$ CFU/mg protein.
°12.5 U/ml recombinant human GM-CSF were added every 48 h; specific activity $5 \times 10^7$ CFU/mg protein.

TABLE IV

Total CFU-GM Production by CD34+, DR−, CD71−
Cells after Addition of Various Cytokines

| Cytokine | Week 1 | 2 | 3 | 4 | 5 | 6 | 8 |
|---|---|---|---|---|---|---|---|
| | CFU-GM/ml culture | | | | | | |
| None | 15 | 4 | 0 | 0 | 0 | 0 | 0 |
| IL-1* | 20 | 0 | 0 | 0 | 0 | 0 | 0 |
| IL-3+ | 664 | 272 | 96 | 448 | 119 | 0 | 0 |
| IL-6§ | 51 | 14 | 0 | 0 | 0 | 0 | 0 |
| GM-CSF° | 402 | 360 | 135 | 28 | 0 | 0 | 0 |
| IL-1/IL-3 | 347 | 324 | 342 | 334 | 167 | 240 | 214 |

Total CFU-GM = CFU-GM/ml culture $(\frac{1}{2})^n$, where n = number of previous demi-populations.
Cells were seeded at $5 \times 10^3$/ml. CFU-GM in initial (day 0) population = 690/5 × $10^3$ cells. Colonies grown in methylcellulose containing 50 U/ml GM-CSF and enumerated after 14 d.
*2.5 U/ml recombinant human IL-1a were added every 48 h; specific activity $10^8$ CFU/mg protein.
+50 U/ml recombinant human IL-3 were added every 48 h; specific activity $10^8$ CFU/mg protein.
§75 U/ml recombinant human IL-6 were added ever 48 h; specific activity $10^7$ CFU/mg protein.
°12.5 U/ml recombinant human GM-CSF were added every 48 h; specific activity $5 \times 10^7$ CFU/mg protein.

TABLE V

Assayable CFU-MK in Long-Term Suspension Cultures
of CD34+ DR−CD71− Cells Receiving
a Combination of Il-3 and IL-6

| Days in culture* | CFU-MK/ml culture+ |
|---|---|
| 7 | 42.6 ± 7.6§ |
| 14 | 67.6 ± 56.6 |
| 21 | 17.0 ± 11.8 |
| 28 | 20.2 ± 10.4 |

50 U/ml recombinant human IL-3 were added every 48 h; specific activity $10^8$ CFUc/mg protein. 75 U.ml recombinant human IL-6 were added every 48 h; specific activity $10^7$ CFU/mg protein.
*Cultures were demi-depopulated every 7 d.
+CFU-MK were assayed in serum-free fibrin clot culture containing 100 U/ml IL-3 colonies enumerated at days 18–24 of culture.
§Each point represents the mean ± SD of triplicate assays.
Values are not corrected for the effects of demi-depopulated.

TABLE VI

Total CFU/GM and BFU-E Production by Sorted Cell
Populations Stimulated with a Combination of IL-3 and IL-6

| Population | Week 1 | 2 | 3 | 4 | 6 | 8 |
|---|---|---|---|---|---|---|
| | CFU-GM (BFU-E) ml cultures | | | | | |
| CD34+DR−CD15− | 275(10) | 286(4) | 64 | 32 | 75 | 0 |
| CD34+DR−CD15+ | 7(1) | 26 | 0 | 0 | 0 | 0 |
| CD34+DR−CD71− | 220(5) | 330(4) | 132 | 18 | 43 | 0 |
| CD34+DR−CD71+ | 13 | 16 | 0 | 0 | 0 | 0 |

Total CFU = CFU/ml culture/$(\frac{1}{2})^n$ = number of previous demi-depopulations. 50 U/ml recombinant human IL-3, specific activity $10^8$ CFU/mg protein and 75 U.ml recombinant human IL-6, specific activity $10^7$ CFU/mg protein were added every 48 h. Cells were seeded at $5 \times 10^3$/ml.

TABLE VII

Differential Analysis of CD34+, DR−, CD15−
Cells after Addition of Various Cytokines

| Cytokines | Day | Blasts | Pro | Myelo | MM | Band % | Seg | Eo | Baso | E | Mo |
|---|---|---|---|---|---|---|---|---|---|---|---|
| Control | 7 | 100 | | | | | | | | | |
| IL-1α* | 7 | 100 | | | | | | | | | |
|  | 14 | 78 | | | | | | | | | 22 |
| IL-6+ | 7 | 100 | | | | | | | | | |
|  | 14 | 27 | 11 | | 9 | | 13 | | 38 | | 2 |
|  | 21 | 9 | | | 48 | 2 | 7 | | 17 | | 17 |
|  | 28 | | | | 30 | | 4 | | | | 66 |
| GM-CSF§ | 7 | 25 | 24 | | 27 | 3 | 21 | | | | |
|  | 14 | 9 | 1 | | 46 | 3 | 21 | | 13 | | 7 |
|  | 21 | 3 | 2 | 1 | 62 | 3 | 5 | | 22 | | 2 |
|  | 28 | 6 | | 1 | 43 | 7 | 3 | | 6 | 2 | 32 |
|  | 35 | | | | 4 | | | | | | 96 |
|  | 42 | | | | 1 | | | | | | 99 |
| IL-3° | 7 | 21 | 44 | | 35 | | | | 1 | | |
|  | 14 | 7 | 7 | | 53 | | | | 33 | | |
|  | 21 | 8 | | | 44 | | | | 48 | | |
|  | 28 | 5 | | | 35 | 3 | 9 | | 35 | | 13 |
|  | 35 | 2 | | | 16 | 5 | 20 | | 25 | | 32 |
|  | 42 | | | | 15 | | 2 | | 20 | | 63 |
| IL-1α/IL-3 | 7 | 1 | 5 | 1 | 53 | 12 | 14 | | 14 | | |
|  | 14 | 5 | | | 34 | 9 | | | 52 | | |
|  | 21 | 1 | | | 53 | 4 | 3 | | 31 | | 8 |

TABLE VII-continued

Differential Analysis of CD34+, DR−, CD15−
Cells after Addition of Various Cytokines

| Cytokines | Day | Blasts | Pro | Myelo | MM | Band % | Seg | Eo | Baso | E | Mo |
|---|---|---|---|---|---|---|---|---|---|---|---|
| | 28 | 1 | | | 42 | 12 | 5 | | 32 | | 8 |
| | 35 | | | | 20 | | | | 27 | | 53 |
| | 42 | | | | 8 | | | | 8 | | 84 |
| | 56 | | | | | | | | 11 | | 89 |
| IL-6/IL-3 | 7 | 19 | 26 | 2 | 40 | 5 | 4 | | 4 | | |
| | 14 | 2 | 2 | | 46 | 3 | 1 | | 46 | | |
| | 21 | 5 | 1 | | 37 | 1 | 7 | | 48 | | 1 |
| | 28 | 4 | 1 | | 37 | 10 | 8 | | 35 | | 5 |
| | 42 | 1 | | | 8 | | 1 | | 9 | | 81 |
| | 56 | | | | 2 | | | | 3 | | 95 |

Differential cell counts were performed on Wright-Giesma stained cytocentrifuge preparations of cells removed from liquid culture. 200 cells per sample were classified; if <200 cells appeared on a slide, all were classified. Abbreviations: Pro, promyelocytes; Myelo, myelocytes; MM, metamyelocytes; Band, neutrophil band form; Seg, segmented neutrophils; Eo, eosinophils; Baso, basophils; E, erythrocytes; and Mo, monocytes. *2.5 U/ml recombinant human IL-1a were added every 48 h; specific activity $10^8$ CFU/mg protein. +50 U/ml recombinant human IL-3 were added every 48 h; specific activity $10^8$ CFU/mg protein. §75 U/ml recombinant human IL-6 were added every 48 h; specific activity $10^7$ CFU/mg protein. °12.5 U/ml recombinant human GM-CSF were added every 48 h; specific activity $5\times10^7$ CFU/mg protein.

EXAMPLE 2

Long-term bone marrow cultures (LTBMC) were initiated with $5\times10^3$ CD34+DR−CD15− marrow cells/ml in the absence of an adherent cell layer to which murine mast cell growth factor (MGF) alone or in combination with IL-3 or a GM-CSF/IL-3 fusion protein (FP: Williams et al. Exp. Hematol. 18: 615, 1990) were added every 48 hours. In cultures not receiving cytokines, viable cells were not detectable after two weeks while cultures receiving IL-3, FP, or MGF sustained hemotopoiesis for 10 weeks. Addition of IL-3 or FP alone increased cell numbers by $10^3$ fold by day 56, while the combination of MGF and FP expanded cell

TABLE VIII

Differential Analysis of CD34+, DR−, CD71−
Cells after Addition of Varios Cytokines

| Cytokines | Day | Blasts | Pro | Myelo | MM | Band % | Seg | Eo | Baso | E | Mo |
|---|---|---|---|---|---|---|---|---|---|---|---|
| Control | 7 | 90 | | | | | | | | | 10 |
| | 14 | 40 | | | | | | | | | 60 |
| IL-1α* | 7 | 82 | | | | | | | | | 18 |
| IL-6+ | 7 | 43 | 4 | | | | | | | | 13 |
| | 14 | 33 | 20 | | | | | | | | 47 |
| GM-CSF§ | 7 | 39 | 33 | | 9 | 5 | 6 | | 5 | | 2 |
| | 14 | 18 | 5 | | 42 | 3 | 12 | | 20 | | |
| | 21 | 4 | | 1 | 66 | 9 | 7 | | | | 4 |
| | 28 | 2 | | | 61 | 3 | 1 | 8 | | | 24 |
| | 35 | 14 | | | 18 | 8 | 8 | 9 | | | 52 |
| | 42 | | | | | | | | | | 100 |
| IL-3° | 7 | 52 | 40 | | 1 | 2 | 2 | | 2 | 1 | |
| | 14 | 29 | 26 | | 26 | 2 | 3 | | 14 | | |
| | 21 | 13 | 4 | 2 | 28 | 2 | 3 | | 48 | | |
| | 28 | 14 | 3 | | 35 | 5 | 1 | | 35 | | 7 |
| | 35 | 9 | | | 20 | 7 | 6 | | 27 | | 31 |
| | 42 | 2 | | | 5 | | 4 | | 16 | 2 | 71 |
| IL-1α/IL-3 | 7 | | 48 | 42 | | 6 | 2 | 1 | | 2 | |
| | 14 | 4 | 1 | 53 | 4 | 5 | | 33 | | | |
| | 21 | 3 | | | 44 | 1 | 1 | | 49 | | 2 |
| | 28 | 21 | 3 | | 34 | 4 | 3 | 1 | 27 | | 8 |
| | 35 | 3 | | | 23 | 4 | 29 | | 20 | | 21 |
| | 42 | 1 | | | 7 | 3 | 3 | | 16 | | 70 |
| | 56 | | | | | | 1 | | 8 | | 91 |

Differential cell counts were performed on Wright-Giesma stained cytocentrifuge preparations of cells removed from liquid culture. 200 cells per sample were classified; if <200 cells appeared on a slide, all were classified. Abbreviations as in Table VII. *2.5 U/ml recombinant human IL-1a were added every 48 h; specific activity $10^8$ CFU/mg protein. +50 U/ml recombinant human IL-3 were added every 48 h; specific activity $10^8$ CFU/mg protein. §75 U/ml recombinant human IL-6 were added every 48 h; specific activity $10^7$ CFU/mg protein. °12.5 U/ml recombinant human GM-CFS were added every 48 h; specific activity $5\times10^7$ CFU/mg protein.

numbers $10^5$-fold ($5\times10^3$ cells at day 0; $5.5\times10^3$ at day 56). Over the 10 week period of LTBMC, treatment with various cytokines led to the following cumulative increases over an input of 213 total assayable hematopoietic progenitor cells (HPC; CFU-GM+BFU-E+CFU-MK): IL-3, 868; FP, 1,265; MGF, 2,006; MGF+IL-3, 4,845; MGF+FP, 155,442. LTBMCs receiving MGF alone possessed a higher HPC cloning efficiency than those receiving IL-3 or FP and its addition increased the cloning efficiencies of cultures containing of IL-3 and FP. The presence of MGF did not increase the longevity of cultures receiving these cytokines.

TABLE IX

Total Cell Production of CD34+, DR−, CD15− Cells after Addition of Various Cytokines

| Cytokine | Day 0 Viable Cell count × 10³ | Day 26 Viable Cell count × 10³ | |
|---|---|---|---|
| None | 5 | 0 | |
| *IL-3 | 5 | 140 | 100% |
| +GM-CSF | 5 | 100 | |
| °FP | 5 | 1,400 | |
| MGF | 5 | 520 | |
| GM-CSF/IL-3 | 5 | 560 | |
| MGF/GM-CSF | 5 | 12,500 | 20% |
| MGF/IL-3 | 5 | 1,200 | |
| MGF/FP | 5 | 10,000 | |

Total cells/ml culture/½Yn = number of previous cell dilutions.
Cultures were periodically split to allow for cellular expension and to perform several analyses at different time points.
*500 pg/ml recombinant human IL-3 was added every 48 hours
+200.0 pg/ml recombinant human GM-CSF was added every 48 hours
°10.0 ng/ml of recombinant GM-CSF-IL-3 fusion protein was added each day
100.0 ng/ml of murine recombinant stem cell factor (SCGF) was added every 48 hours

TABLE X

Differential Analysis of CD34+, DR−, CD15− Cells After Addition of Various Cytokines on Day 26 of Suspension Culture

| Cytokines | Blasts | Pro | Myelo | MM | Band | Seg | Lymph | Eo | Baso | Mo | Norm |
|---|---|---|---|---|---|---|---|---|---|---|---|
| FP | 3 | 7 | 9 | 9 | 27 | 3 | 5 | 2 | 9 | 0 | 5 |
| GM-CSF/IL-3 | 1 | 7 | 4 | 13 | 24 | 32 | 4 | 3 | 4 | 0 | 0 |
| MGF | 32 | 4 | 9 | 9 | 13 | 12 | 7 | 1 | 1 | 12 | 0 |
| MGF/GM-CSF | 21 | 10 | 15 | 12 | 14 | 7 | 5 | 2 | 3 | 11 | 0 |
| MGF/IL-3 | 38 | 3 | 15 | 12 | 13 | 4 | 2 | 2 | 4 | 7 | 2 |
| MGF/FP | 37 | 17 | 16 | 9 | 9 | 5 | 1 | 0 | 6 | 0 | 5 |

Differential cell counts were performed on Wright Giemsa stained cytocentrifuge preparations of cells removed from liquid culture. 200 cells per sample. Abbreviation used, Norm, normoblasts, other abbreviations as in Table VII. Cytokines were added at same dose as detailed in legend of Table I.

Numerous modifications and variations of the present invention are possible in light of the above teachings; therefore, within the scope of the appended claims the invention may be practiced otherwise than as particularly described.

EXAMPLE 3

Liquid-culture systems supplemented with repeated 48 hourly cytokine additions was utilized to study cell populations cultured from two donors. Total cell production of CD34+DR−CD15− cells is shown in Table XI while assayable CFU-GM in these cultures over time is recorded in Table XIII. In the absence of exogenous cytokines, total cell numbers declined over a 1 to 2-wk period and assayable CFU-GM persisted for only a 1 to 2-wk period. In donor 1, MGF/FP cytokine combination promoted increased total cell production for 8 wk, by which time cell numbers represented over 110×10³ times the number present in the initial seeding populations. In donor 2 the same cytokine combination promoted increased total cell production for 6 wk, by which time the cell numbers represented by over 16×10³ times the number present in the initial seeding population. Assayable CFU-GM for donor 1 and donor 2 cultured with MGF/FP cytokine combination persisted for 6-8 wk and 3-4 wk, respectively and significantly surpassed the CFU-GM population initially assayable.

The cytokine combination MGF/IL-3 promoted over 2×10³ fold increase in total cell production over the initial seeding for donor 1 at 6 wk and donor 2 at 8 wk. Additionally, viable cell counts remain high through 10 wk. The assayable expansion of CFU-GM for donor 1 and 2 cultured with MGF/IL-3 cytokine combination persisted for 6-8 wk for each donor and each significantly surpassed the CFU-GM population assayable initially.

Total BFU-E production by CD34+DR−CD15− cells is shown in Table XIV. In donor 1 and donor 2 the cytokine combination MGF/FP persisted for 1-2 wk and 3-4 wk, respectively with only donor 2 showing a significant increase over the BFU-E population initially assayable. The cytokine combination MGF/IL-3 persisted in Donor 1 for 2-3 wk and in donor 2 for 3-4 wk, with both showing significant increase in wk 1-2 over the BFU-E population initially assayable. Total CFU-MK production by CD34+DR−CD15− cells is shown in Table XV. The cytokine combination of MGF/IL-3 for both donor 1 and 2 show CFU-MK persistance for through 10 wk and each has significantly surpassed the initially assayable CFU-MK population. Donors 1 and 2 show CFU-MK persistance for 6-8 wk and 8-10 wk, respectively, both showing significant increases over the initial CFU-MK population.

Morphological analysis of the cells in the suspension cultures of donor 1 during the period of observation revealed changes in the cellular composition of the population following the addition of various cytokines, see Table XII, which shows the differential analysis of CD34+DR−CD15− cells. Cultures receiving MGF/FP were composed of 11% blasts by 14 days and cultures receiving MGF/IL-3 were composed of 17% blasts by 14 days. The highest percentage of blasts by 14 days was in the cultures receiving MGF alone which were composed of 30% blasts. In contrast IL-3 and FP containing cultures had reduced the percentage of blasts cells appreciably by day 14.

Table XVI depicts the percentage of total cells which give rise to progenitor cells of colony forming units. Although MGF percentages are high the overall expansion of cultures receiving MGF is not as substantial, however the cultures receiving MGF/IL-3 cytokines provide high plating percentages and substantial overall expansion (see Tables XI-XV)

TABLE XI

Total Cell Production of CD34+, DR−, CD15− Cells Cultured in the Absence of Various Cytokines
Viable cell count × 10³/ml

| Cytokine | Week 1 | 2 | 3 | 4 | 6 | 8 | 10 |
|---|---|---|---|---|---|---|---|
| Donor 1 | | | | | | | |
| None | 1 | 0 | 0 | 0 | 0 | 0 | 0 |

TABLE XI-continued

Total Cell Production of CD34+, DR−, CD15−
Cells Cultured in the Absence of Various Cytokines
Viable cell count × 10³/ml

| Cytokine | Week 1 | 2 | 3 | 4 | 6 | 8 | 10 |
|---|---|---|---|---|---|---|---|
| IL-3[1] | 28 | 144 | 271 | 560 | 480 | 762 | 960 |
| GM-CSF[2] | 12 | 107 | 436 | 1,085 | 2,680 | 2,080 | 1,760 |
| IL-3/GM-CSF | 23 | 244 | 742 | 1,620 | 1,979 | 2,035 | 2,720 |
| FP[3] | 42 | 262 | 587 | 1,240 | 3,000 | 1,494 | 480 |
| MGF[4] | 8 | 104 | 933 | N.D.[5] | 1,680 | 1,760 | 640 |
| MGF/FP | 101 | 1,211 | 35,100 | 101,000 | 262,400 | 550,000 | 100,000 |
| MGF/IL-3 | 38 | 213 | 978 | 2,820 | 10,800 | 3,680 | 5,120 |
| Donor 2 | | | | | | | |
| None | 1 | 0 | 0 | 0 | 0 | 0 | 0 |
| IL-3 | 24 | 180 | 650 | 605 | 1,400 | 960 | 864 |
| FP | 41 | 810 | 2,100 | 6,680 | 1,840 | 4,320 | 5,280 |
| MGF | 8 | 27 | 71 | 98 | 230 | 70 | 0 |
| MGF/FP | 100 | 1,280 | 15,700 | 6,400 | 81,000 | 19,520 | 0 |
| MGF/IL-3 | 36 | 305 | 780 | 1,380 | 6,960 | 10,400 | 5,440 |
| Donor 3 | | | | | | | |
| MGF/FP | N.D. | 5,040 | 14,400 | 14,800 | 8,960 | | |

Total cells = cells/ml culture/(n)ⁿ where n = number of demi-depopulations.
Cultures were seeded at 5 × 10³ cells/ml.
[1]500 pg/ml recombinant human IL-3 was added every 48 hours; specific activity 3.5 × 10⁸ CFU/mg protein
[2]250 pg/ml recombinant human GM-CSF was added every 48 hours; specific activity 2 × 10⁸ CFU/mg protein.
[3]10 ng/ml recombinant human FP was added every 48 hours; specific activity 1-2 × 10⁸ CFU/mg
[4]50 ng/ml recombinant murine MGF was added every 48 hours; specific activity 10⁶ CFU/mg protein
[5]N.D. — not determined.

TABLE XII

Differential Analysis of CD34+ DR− CD15− Cells following Culture with Various Cytokines

| Cytokines | Day | Blasts % | Pro | Myelo | Meta | Band | Seg | Baso | Eos | Mono |
|---|---|---|---|---|---|---|---|---|---|---|
| Post Sort | 0 | 82 | 1 | 1 | | | | 6 | | 10 |
| IL-3[1] | 7 | 10 | 8 | 16 | 2 | | 9 | 50 | 2 | 3 |
| | 14 | 2 | 4 | 39 | 4 | 3 | 10 | 28 | | 10 |
| | 28 | 3 | 6 | 13 | 3 | 1 | 6 | 61 | | 7 |
| FP[2] | 7 | 10 | 21 | 52 | 5 | | 2 | 7 | | 3 |
| | 14 | 1 | 4 | 17 | 8 | 3 | 20 | 14 | | 33 |
| | 28 | | 1 | 24 | 7 | 4 | 36 | 8 | | 20 |
| MGF[3] | 7 | 54 | 39 | 3 | | | | 1 | | 3 |
| | 14 | 30 | 38 | 9 | 1 | 1 | | 1 | | 20 |
| | 28 | 1 | 7 | 21 | 18 | 13 | 15 | 1 | 1 | 23 |
| MGF/FP | 7 | 29 | 22 | 23 | 3 | | 4 | 18 | | 1 |
| | 14 | 11 | 22 | 16 | 4 | 2 | 4 | 13 | | 28 |
| | 28 | 1 | 8 | 13 | 12 | 2 | 10 | 2 | | 52 |
| MGF/IL-3 | 7 | 31 | 15 | 48 | | | 2 | 4 | | |
| | 14 | 17 | 14 | 9 | 2 | 4 | 8 | 34 | | 12 |
| | 28 | | 8 | 46 | 17 | 2 | 17 | 2 | | 8 |

Differential cell counts were performed on Wright-Giemsa-stained cytocentrifuge preparations of cells removed from liquid culture. ≧100 cells per sample were classified. Abbreviations: Pro, promyelocyte; Myelo, myelocyte; Meta, metamyelocyta; Band, neutrophil band form; Seg, segmented neutrophil; Baso, basophil; Eos, eosinophil; Mono, monocyte.
[1]500 pg/ml recombinant human IL-3, specific activity 3.5 × 10² CFU/ml protein
[2]10 ng/ml recombinant human FP, specific activity 1-2 × 10³ CFU/mg protein
[3]50 ng/ml recombinant murine MGF, specific activity 10⁶ CFU/mg protein

TABLE XIII

Total CFU-GM Production by CD34+ DR− CD15− Cells Cultured in the Presence of Various Cytokines
CFU-GM/ml culture[1]

| Cytokine | Week 1 | 2 | 3 | 4 | 6 | 8 |
|---|---|---|---|---|---|---|
| Donor 1 | | | | | | |
| None | 8 | 0 | 0 | 0 | 0 | 0 |
| IL-3[2] | 132 | 28 | 80 | N.D.[5] | N.D. | 128 |
| GM-CSF[3] | 192 | 112 | 88 | N.D. | 128 | 0 |
| IL-3/GM-CSF | 196 | 104 | 36 | N.D. | 128 | 576 |
| FP[4] | 86 | 112 | 128 | 176 | N.D. | 64 |
| MGF[5] | 290 | 396 | 608 | 448 | 96 | 0 |
| MGF/FP | 376 | 1,600 | 14,800 | 38,000 | 80,000 | 0 |
| MGF/IL-3 | 144 | 348 | 104 | 416 | 2,528 | 192 |
| Donor 2 | | | | | | |
| None | 0 | 0 | 0 | 0 | 0 | N.D. |
| IL-3 | 232 | 196 | 96 | 16 | 64 | N.D. |
| FP | 84 | 148 | 288 | 320 | 544 | N.D. |
| MGF | 106 | 152 | 360 | 64 | 128 | N.D. |
| MGF/FP | 114 | 1,440 | 10,600 | N.D. | N.D. | N.D. |
| MGF/IL-3 | 62 | 240 | 504 | 32 | 1,024 | N.D. |
| Donor 3 | | | | | | |
| MGF/FP | N.D. | 12,448 | 32,264 | 32,264 | 1,254 | 0 |

Total CFU-GM = CFU-GM/ml culture/(n)ⁿ where n = number of previous demi-depopulations.
[1]Cultures were seeded at 5 × 10³ cells/ml. CFU-GM/5 × 10³ cells in initial population: Donor 1, 150; Donor 2, 227, Donor 3, 144. Colonies grown in methylcellulose containing 500 pg/ml GM-CSF and 1 U human urinary erythropoietin and enumerated after 14 days.
[2]500 pg/ml recombinant human IL-3 was added every 48 hours; specific activity 3.5 × 10⁸ CFU/mg protein.
[3]250 pg/ml recombinant human GM-CSF was added every 48 hours; specific activity 2 × 10⁸ CFU/mg protein.
[4]10 ng.ml recombinant human FP was added every 48 hours; specific activity 1-2 × 10³ CFU/mg protein.
[5]ng/ml recombinant murine MGF was added every 48 hours; specific activity 10⁶ CFU/mg protein.
[6]N.D. — not determined.

TABLE XIV

Total BFU-E Production by CD34+ DR− CD15− Cells Cultured in the Presence of Various Cytokines BFU-E/ml culture[1]

| Cytokine | Week 1 | 2 | 3 | 4 |
|---|---|---|---|---|
| Donor 1 | | | | |
| None | 0 | — | — | — |
| IL-3 | 24 | 0 | 0 | 0 |
| GM-CSF | 8 | 0 | 0 | 0 |
| IL-3/GM-CSF | 22 | 4 | 0 | 0 |
| FP | 20 | 4 | 0 | 0 |
| MGF | 8 | 40 | 0 | 0 |

TABLE XIV-continued

Total BFU-E Production by CD34+ DR− CD15− Cells
Cultured in the Presence of Various Cytokines
BFU-E/ml culture[1]

| Cytokine | Week 1 | 2 | 3 | 4 |
|---|---|---|---|---|
| MGF/FP | 98 | 0 | 0 | 0 |
| MGF/IL-3 | 238 | 4 | 0 | 0 |
| *Donor 2* | | | | |
| C | 0 | — | — | — |
| IL-3 | 40 | 28 | 0 | 0 |
| FP | 132 | 68 | 56 | 16 |
| MGF | 6 | 0 | 0 | 0 |
| MGF/FP | 662 | 100 | 200 | 0 |
| MGF/IL-3 | 1,062 | 272 | 40 | 0 |

Total BFU-E - BFU-E/ml culture/(N)$^n$ where n = number of previous demi-depopulations.
[1] Cultures were seeded at 5 × 10³ cells/ml. Each point represents the mean of two separate experiments. Mean BFU-E/5 × 10³ cells in initial population: = Donor 1, 173; Donor 2, 154. Colonies grown in methylcellulose containing 500 pg/ml GM-CSF and 1 U human urinary erythropoietin and enumerated at 12 days.
[2] 500 pg/ml recombinant human IL-3 added every 48 hours; specific activity 3.5 × 10⁶ CFU/mg protein.
[3] 250 pg/ml recombinant human GM-CSF added every 48 hours; specific activity 2 × 10⁸ CFU/mg protein.
[4] 10 ng/ml recombinant human FP[ added every 48 hours; specific activity 1-2 × 10⁸ CFU/mg protein.
[5] 50 ng/ml recombinant murine MGF added every 48 hours; specific activity 10⁸ CFU/mg protein.

TABLE XV

Total CFU-MK Production by CD34+ DR− CD15−
Cells Cultured in the Presence of Various Cytokines
CFU-MK/ml culture[1]

| Cytokine | Week 2 | 3 | 4 | 5 | 8 | 10 |
|---|---|---|---|---|---|---|
| *Donor 1* | | | | | | |
| None | 0 | 0 | 0 | 0 | 0 | 0 |
| IL-3[2] | 14 | 74 | 100 | 118 | 48 | N.D.[6] |
| GM-CSF[3] | 12 | 40 | 20 | 48 | 32 | 0 |
| IL-3/GM-CSF | 20 | 80 | 96 | 120 | N.D. | N.D. |
| FP[4] | 28 | 120 | 184 | 118 | 96 | 64 |
| MGF[5] | 6 | 12 | 36 | 20 | 0 | 0 |
| MGF/FP | 40 | 120 | 120 | 120 | N.D. | 0 |
| MGF/IL-3 | 26 | 90 | 208 | 220 | 128 | 64 |
| *Donor 2* | | | | | | |
| None | 8 | 0 | 0 | 0 | 0 | 0 |
| IL-3 | 26 | 100 | 140 | 140 | 64 | 64 |
| GM-CSF | 24 | 40 | 60 | 80 | 32 | 0 |
| IL-3/GM-CSF | 40 | 120 | 160 | 200 | 64 | 64 |
| FP | 56 | 120 | 200 | 200 | 96 | 64 |
| MGF | 10 | 3 | 60 | 60 | 0 | 0 |
| MGF/FP | 56 | 200 | 200 | 200 | 40 | 0 |
| MGF/IL-3 | 34 | 120 | 240 | 260 | 160 | 192 |

Total CFU-MK - CFU-MK/ml culture/(N)$^n$ where n = number of previous demi-depopulations.
[1] Cultures were seeded at 5 × 10³ cells/ml. Each point represents the mean of two separate experiments. Mean CFU-MK/5 × 10³ cells in initial populations = 0. Colonies cultured in fibrin clot containing 1 ng IL-3 and enumerated at 15 days.
[2] 1 ng/ml recombinant human IL-3 was added every 48 hours; specific activity 3.5 × 10³ CFU/mg protein.
[3] 200 pg/ml recombinant human GM-CSF was added every 48 hours; specific activity 2 × 10⁸ CFU/mg protein.
[4] 10 ng/ml recombinant human FP was added every 48 hours; specific activity 1-2 × 10⁸ CFU/mg protein.
[5] 100 ng/ml recombinant murine MGF was added every 48 hours; specific activity 10⁶ CFU/mg protein.
[6] Not determined.

| Cytokine | Week 1 | 2 | 3 | 4 | 6 | 8 |
|---|---|---|---|---|---|---|
| | % plating Efficiency[1] | | | | | |
| None | N.D.[6] | — | — | — | — | — |
| IL-3[2] | 0.86 | 0.072 | 0.023 | 0.003 | 0.005 | 0.009 |
| GM-CSF[3] | 1.67 | 0.105 | 0.020 | N.D. | 0.005 | 0.000 |
| IL-3/GM-CSF | 0.96 | 0.044 | 0.005 | N.D. | 0.006 | 0.028 |
| FP[4] | 0.42 | 0.039 | 0.019 | 0.010 | 0.015 | 0.002 |
| MGF[5] | 2.58 | 0.493 | 0.580 | 0.065 | 0.031 | 0.000 |
| MGF/FP | 0.65 | 0.127 | 0.056 | 0.029 | 0.015 | 0.000 |
| MGF/IL-3 | 2.10 | 0.173 | 0.041 | 0.008 | 0.019 | 0.002 |

[1] % Plating Efficiency = colonies enumerated/cells cultured × 100%. Cells at each timepoint were counted and cultured in methylcellulose containing 500 pg GM-CSF and 1 U human urinary erythropoietin or in fibrin clot containing 1 ng IL-3 and enumerated at 14 days. Each point represents the mean of two to four separate experiments. Mean cloning efficiency of initial (day 0) population: 4.54%
[2] 500 pg/ml recombinant human IL-3 was added every 48 hours; specific activity 3.5 × 10⁸ CFU/mg protein
[3] 200 pg/ml recombinant human GM-CSF was added every 48 hours; specific activity 2 × 10⁸ CFU/mg protein.
[4] 10 ng/ml recombinant human FP was added every 48 hours; specific activity 1-2 × 10⁸ CFU/mg protein.
[5] 100 ng/ml recombinant murine MGF was added every 48 hours; specific activity 10⁸ CFU/mg protein.
[6] N.D. — Not determined.

EXAMPLE 4

Serum-free long-term suspension human bone marrow culture system. Serum-free media was prepared as previously outlined by Ponting et al. (19). Both serum-free and serum-containing cultures were initiated with CD34+DR−CD15− cells and supplemented every 48 hours with KL and a GM-CSF/IL-3 fusion molecule (FP).

As can be seen in Table XVII, cultures maintained in serum-free media were characterized by far less total cell production than has been observed in comparable serum containing culture. Over the 6 weeks of observation, these LTBMCs exhibited a mere 24-fold increase in total cell numbers, yet were characterized by a 6-fold increase in CFU-GM and a 1.8-fold increase in HPP-CFC. Remarkably, however, the progenitor cell cloning efficiency in serum-free cultures was 1.4% after 28 days of LTBMC (Table XVII) in comparison to a cloning efficiency of 0.03% in comparable serum-containing cultures. These studies suggest that the serum-free culture system is preferred for expanding progenitor cell numbers at the expense of impairing the production of more differentiated cells.

TABLE XVII*

| Day in Culture | Cell No. × 10³ | Progenitor Cells | |
|---|---|---|---|
| | | CFU-GM | HPP-CFC |
| 0 | 10 | 375 | 40 |
| 14 | 30 | 744 | 9 |
| 28 | 70 | 1,050 | 21 |
| 42 | 140 | 140 | 42 |

*CD34+ DR− CD15− cells were susp]ended in serum-free medium and supplemented with 100 ng/ml of KL and 10 ng/ml of FP every 48 hours.

References:
1. Gordon, M. Y., C. R. Dowding, G. P. Riley, and M. F. Greaves. 1987. Characterization of stroma-dependent blast colony-forming cells in human marrow. J. Cell. Physiol 120:150–156.
2. Brandt, J. E., N. Baird, L. Lu, E. Srour, and R. Hoffman. 1988. Characterization of a human hematopoietic progenitor cell capable of forming blast cell containing colonies in vitro. J. Clin. Invest. 82:1017–1027.
3. Dexter, T. M., T. D. Allen, and L. G. Lajtha. 1977. Conditions controlling the proliferation of hematopoietic stem cells in vitro. J. Ce.. Physiol. 91:335–344.
4. Roberts, R. A., E. Spooncer, E. K. Parkinson, B. I. Lord, T. D. Allen, and T. M. Dexter. 1987. Metabolically inactive 3T3 cells can substitute for marrow stromal cells to promote the proliferation and development of multipotent hematopoietic stem cells.. J. Cell. Physiol. 132:203-214.

5. Eliason, J. F., B. Thorens, V. Kindlet, and P. Vassalli. 1988. The roles of granulocyte-macrophage colony-stimulating factor and interleukin-3 in stromal cell-mediated hemopoiesis in vivo. Exp. Hematol. 16:307-312.

6. Strauss, L. C., R. K. Stuart, and C. I. Civin. 1983. Antigenic analysis of hematopoiesis. I. Expression of the My-1 granulocyte surface antigen on human marrow cells and leukemic cell lines. Blood. 61:1222-1231.

7. Sieff, C., D. Bicknell, G. Caine, J. Robinson, G. Lam, and M. F. Greaves. 1982. Changes in cell surface antigen expression during hemopoietic differentiation. Blood. 60:703-713.

8. McNiece, I. K., F. M. Stewart, D. M. Deacon, D. S. Temeles, K. M. Zsebo, S. C. Clark, and P. J. Quesenberry. 1989. Detection of a human CFC with a high proliferative potential. Blood. 74:609-612.

9. Brno, E., R. Briddell, and R. Hoffman. 1988. Effect of recombinant and purified hematopoietic growth factors on human megakaryocyte colony formation. Exp. Hematol. 16:371-377.

10. Moore, M. A. S., and A. P. C. Sheridan. 1979. Pluripotent stem cell replication in continuous human, prosimian, and murine bone marrow culture. Blood Cells. 5:297-311.

11. Hocking, W. G., and D. W. Golde. 1980. Long-term human bone marrow cultures. Blood 56:118-124.

12. Gartner, S., and H. S. Kaplan. 1980. Long-term culture of human bone marrow cells. Proc. Natl. Acad. Sci. USA, 77:4756-4759.

13. Slovick, F. T., C. N. Abboud, .K. Brennan, and M. A. Lichtman. 1984. Survival of granulocytic progenitors in the anonadherent and adherent compartments of human long-term marrow cultures. Exp. Hematol. 12:327-338.

14. Coulombel, L., A. C. Eaves, and C. J. Eaves. 1983. Enzymatic treatment of long-term human marrow cultures reveals the preferential location of primitive hematopoietic progenitor in the adherent layer. Blood 62:291-297.

15. Gordon, M. Y., J. A. Hibben, S. Dowding, E. C. Gordon-Smith, and J. M. Goldman. 1985. Separation of human blast progenitors from granulocytic, erythroid megakaryocytic, and mixed colony forming cells by "panning" on cultures marrow-derived stromal layers. Exp. Hematol. 13:937-940.

16. Li, D. L., and G. R. Johnson. 1985. Stimulation of multipotential, erythroid and other murine hematopoietic progenitor cells by adherent cell lines in the absence of detectable multi-CSF (IL-3). Nature (Lond.). 316:633-636.

17. Tsai, S., C. A. Sieff, and D. G. Nathan. 1986. Stromal cell-associated erythropoiesis. Blood. 67:1418-1426.

18. McNiece, I. K., Langley, K. E., and Zsebo, K. M., 1991. Recombinant Human Stem Cell F actor Synergises with GM-CSF, G-CSF, IL-3 and Epo to Stilulate Human Progenitor Cells of the Myeloid and Erythroid Lineages, Exp. Hematol., 19:226, 231.

19. Ponting, I. K. D.; Heyworth, C. M.; Cormier, F. and Dexter, T. M., Growth Factors, 4:165-173, 1991.

What is claimed is:

1. A method for growing human hematopoietic stem cells in a liquid culture medium, the method comprising:
   adding said human hematopoietic stem cells to a liquid culture medium essentially free of stromal cells, comprising the cytokine mast cell growth factor (MGF) maintained at a concentration of at least 10 ng/ml, in an amount effective to provide for an expansion in the cell number in said population from at least about 100 fold and not more than about 200 fold within a period of 26 days; and
   growing the population of said human hematopoietic stem cells in said medium.

2. A method according to claim 1, wherein said human hematopoietic stem cells are characterized as being CD34+DR−CD15−.

3. A method for growing human hematopoietic stem cells in a liquid culture medium the method comprising:
   adding said human hematopoietic stem cells to a liquid culture medium essentially free of stromal cells, comprising the cytokine mast cell growth factor (MGF) maintained at a concentration of at least 10 ng/ml, wherein said medium further comprises at least one cytokine selected from the group consisting of interleukin 3 (IL-3) maintained at a concentration from about 500 pg/ml; granulocyte macrophage colony stimulating factor (GM-CSF) maintained at a concentration from about 100 pg/ml and IL-3/GM-CSF fusion protein maintained at a concentration from about 1 ng/ml; in an amount effective to provide for an expansion in the cell number in said population from at least about 100 fold and not more than about 20,000 fold within a period of 26 days; and
   growing the population of said human hematopoietic stem cells in said medium.

4. A method according to claim 3, wherein said cytokines are added to said culture medium every 48 hours.

5. A method for growing human hematopoietic stem cells in a liquid culture medium, wherein said human hematopoietic stem cells are characterized as being CD34+DR−CD15−, the method comprising:
   adding said human hematopoietic stem cells to a medium essentially free of stromal cells, comprising the cytokine mast cell growth factor (MGF) maintained at a concentration of at least about 10 ng/ml, and at least one cytokine selected from the group consisting of interleukin 3 (IL-3) maintained at a concentration from about 0.5 ng/ml; granulocyte macrophage colony stimulating factor (GM-CSF) maintained at a concentration from about 0.2 ng/ml and IL-3/GM-CSF fusion protein maintained at a concentration from about 10 ng/ml; in an amount effective to provide for an expansion in the cell number in said population from at least about 100 fold and not more than about 2,000 fold within a period of 26 days;
   growing the population of said human hematopoietic stem cells in said medium for at least about 26 days.

* * * * *

UNITED STATES PATENT AND TRADEMARK OFFICE
CERTIFICATE OF CORRECTION

PATENT NO. : 5,409,825
DATED     : April 25, 1995
INVENTOR(S) : Ronald Hoffman, et. al.

It is certified that error appears in the above-indentified patent and that said Letters Patent is hereby corrected as shown below:

Title page, item [73], Assignee:  should read--Indiana University Foundation Bloomington, Indiana--

Signed and Sealed this

Ninth Day of April, 1996

Attest:

BRUCE LEHMAN

Attesting Officer         Commissioner of Patents and Trademarks